United States Patent [19]

Linder

[11] Patent Number: 4,774,940
[45] Date of Patent: Oct. 4, 1988

[54] BREATHING CIRCUIT CONNECTOR FOR USE IN ANESTHESIOLOGY

[76] Inventor: Gerald S. Linder, P.O. Box 1085, Pacific Palisades, Calif. 90272

[21] Appl. No.: 504,539

[22] Filed: Jun. 15, 1983

[51] Int. Cl.$^4$ .................. A61M 16/00; F61L 25/00; F61L 43/00
[52] U.S. Cl. .................. 128/204.18; 128/912; 604/283; 604/284; 285/177; 285/179
[58] Field of Search ............ 128/912, 207.14, 207.15, 128/203.11–209.29, 205.24, 204.18, 202.27, 203.12; 604/280–283, 284, 905; 285/177, 243, 179

[56] References Cited

U.S. PATENT DOCUMENTS

| | | | |
|---|---|---|---|
| 1,777,120 | 9/1930 | Lewin | 285/177 |
| 3,552,778 | 1/1971 | Muller | 128/912 |
| 3,616,799 | 11/1971 | Sparks | 128/207.15 |
| 3,918,450 | 11/1975 | Patel | 128/912 |
| 4,111,197 | 9/1918 | Warncke et al. | 128/202.27 |
| 4,152,017 | 5/1979 | Abramson | 128/207.14 |
| 4,331,142 | 5/1982 | Degen | 128/207.15 |
| 4,369,991 | 1/1983 | Linder | 285/179 |
| 4,378,795 | 4/1983 | Feathers et al. | 128/912 |
| 4,416,273 | 11/1983 | Grimes | 128/912 |

FOREIGN PATENT DOCUMENTS

| | | | |
|---|---|---|---|
| 2137788 | 12/1972 | France | 128/202.27 |
| 906587 | 9/1962 | United Kingdom | 128/205.24 |

OTHER PUBLICATIONS

Ohio Chemical Hospital Equipment and Medical Gases, "Endotracheal Tube Adaptors", *Anesthesia Apparatus and Accessories Catalog*, Jul. 20, 1966, p. 44.

Primary Examiner—Kyle L. Howell
Assistant Examiner—K. M. Reichle
Attorney, Agent, or Firm—B. F. Spencer

[57] ABSTRACT

A breathing circuit connector for intercoupling between the flexible hoses of an anesthesiology machine and the input connector of an endotracheal tube is disclosed. The breathing circuit connector consists of a hollow body of relatively rigid material having a cylindrical male input section and a cylindrical female output section. A cylindrical bore within the hollow body extends between the cylindrical input and output sections. The bore within the cylindrical output section consists of a series of two or more cylindrical portions having different internal diameters. The internal diameter of the first bore portion adjacent the output end of the cylindrical output section is slightly larger than the internal diameter of the bore portion situated within the cylindrical output section. The breathing circuit connector may be formed as an elbow with the longitudinal axis of the bore of the cylindrical output section being inclined relative to the longitudinal axis of the bore of the cylindrical input section. Alternatively, the improved connector may comprise a single female output section and a pair of cylindrical male sections, each section having a bore whose axis is displaced from the other to form a Y-shaped connector.

6 Claims, 6 Drawing Sheets

4,774,940

BREATHING CIRCUIT CONNECTOR FOR USE IN ANESTHESIOLOGY

BACKGROUND OF THE INVENTION

The present invention relates to connectors, and, in particular, to an improved breathing circuit connector for intercoupling between the flexible hoses of an anesthesiology machine and the input of an endotracheal tube connector.

The conventional breathing circuit connector consists of a hollow cylindrical body of rigid or semi-rigid plastic material having a straight or tapered male input section, a normally straight female output section, and a cylindrical bore extending between the input and output sections or ends. The connector may be shaped as an elbow with the longitudinal axis of the bore portion within the input section being displaced 90° from the longitudinal axis of the bore portion within the output section. Alternatively, the bore may extend in a straight line or it may be curved. Another type of breathing circuit connector consists of a single female output section and a pair of male cylindrical sections displaced from each other, the connector being in the shape of a Y. The output female section of the conventional cylindrical breathing circuit connector has a bore of standard, uniform diameter, i.e. fifteen millimeters, and is adapted for coupling to the male input section of an endotracheal tube connector. The male input section of the breathing circuit connector is adapted for insertion either into the flexible, corrugated hose from an anesthesiology machine or for insertion into the output female section of the conventional Y-shaped connector. The two male sections of the conventional Y-shaped connector are securely attached, respectively, to two separate and independent flexible hoses from the anesthesiology machine, as by cementing.

Prior art breathing circuit connectors have been found to possess a rather serious problem in attempting to maintain a secure, air tight coupling between a tapered male input section and a corresponding female output section. When the material forming the male input section is composed of a relatively rigid or semi-rigid plastic or polymer material, such as nylon, polyethylene or polypropylene, a rather strong force is needed to insure that the male input section is firmly inserted into the female output section. Where the female output section has either a straight, uniform, cylindrical internal diameter, or a tapered internal diameter, the coupling between the male and female sections has been found to work loose and, at times, to become completely disconnected. This has been especially true when the material forming the female output section is also composed of a relatively hard or semi-rigid material. The failure of the breathing circuit connection, either during an operation or in post-operative recovery, represents a very serious hazard to the health of the patient. The same danger exists where the female output section of the conventional elbow, or 90° breathing circuit connector, is coupled to a tapered male input section of the conventional, hard plastic, endotracheal tube connector. The problems also exist between the coupling between the female output section of the conventional Y-shaped breathing circuit connector and the male input section of the conventional endotracheal tube connector.

One solution to the above problem has been to employ bands, cords or adhesive to bind together each connection in the breathing circuit coupling. To facilitate the use of cords or bands, a crown frequently is formed atop the hard plastic breathing circuit connector to serve as a base or anchor to which the bands, cords or adhesive may be attached.

Another solution has been to employ breathing circuit connectors formed of resilient material having a somewhat higher coefficient of friction in the hope that the required air-tight coupling will be retained. With this type of connector, it is very difficult to disconnect the coupling, as is often required during an operation.

Still another solution has been to employ breathing circuit connectors designed to include an external ridge or ring upon the outside surface of the male input section in norder to engage a mating internal groove formed inside the female section of the connector, as disclosed in the U.S. Pat. Nos. 3,552,778 and 4,152,017.

A partial solution to the above problem has been the introduction of an improved endotracheal tube connector having a male input section consisting of a series of three external stepped diameter portions, as described in my U.S. Pat. No. 4,369,911. This particular endotracheal tube connector has been found to maintain a secure and reliable air-tight coupling to the female output section of the standard fifteen millimeter breathing circuit connector.

The present invention overcomes the above problems by the elimination of the tapered, or the straight bore, of the female output section of the conventional breathing circuit connector. This is achieved by designing the internal bore in the form of a series of straight and uniform internal diameter bore portions of slightly different diameters. This design feature enables one or more of the internal bore portions to seat upon the male input section of the endotracheal tube connector or upon the male input section of the conventional elbow breathing circuit connector in such manner as to reduce the internal forces that normally cause the coupling to separate and, thereby, disconnect.

A principal object of the present invention is to provide a breathing circuit connector having a more secure and reliable air-tight coupling to an endotracheal tube connector.

Another object is to provide a breathing circuit connector which is easier to connect to and to disconnect from an endotracheal tube connector.

A further object is to provide a breathing circuit connector suitable for use with endotracheal tube connectors of different manufacture.

Still another object is to provide a breathing circuit connector capable of achieving an airtight coupling despite small dimensional variations in the material forming the connector.

The above objects of and the brief introduction to the present invention will be more fully understood, and further objects and advantages will become apparent, from a study of the following detailed description in connection with the drawings.

DESCRIPTION OF THE INVENTION

Figure 1:
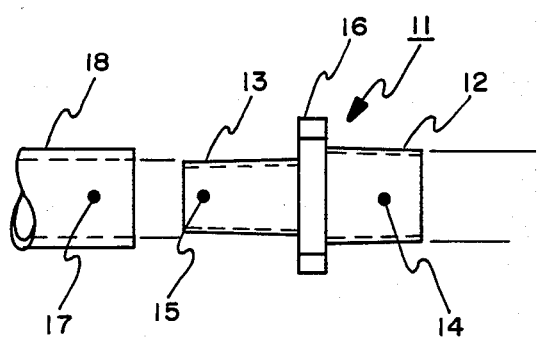
FIG. 1 is a side view of a prior art endotracheal tube connector adapted for insertion into the open proximal end of a conventional endotracheal tube.

FIG. 1 illustrates one type of prior art endotracheal tube connector 11 having a hollow, externally tapered cylindrical input section 12, a hollow externally tapered cylindrical output section 13 and a cylindrical bore 14, 15 extending therebetween. Connector 11 employs a centrally located external flange portion 16 between the input and output sections 12 and 13 to facilitate holding connector 11 between the thumb and fingers by the using physician. The output section 13 is adapted for insertion into the open proximal end 17 of a conventional endotracheal tube 18. The size of output section 13 and bore 15 may vary to accommodate different sizes of endotracheal tubes.

Figure 2:
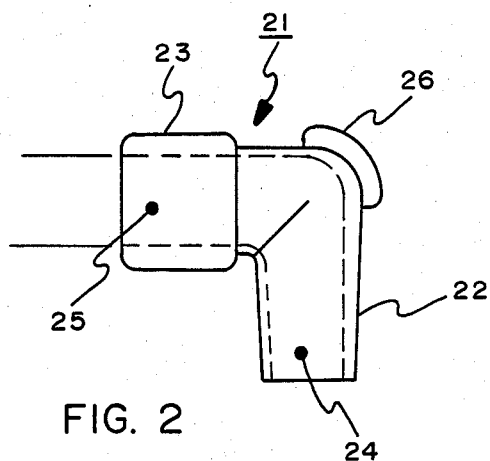
FIG. 2 is a side view of one prior art type of breathing circuit connector for intercoupling between the flexible hoses of an anesthesiology machine and the input to an endotracheal tube connector.

FIG. 2 illustrates one type of prior art breathing circuit connector 21 of the elbow, or 90°, type. Connector 21 usually is composed of a relatively hard plastic material, such as polyethylene, polypropylene, nylon or the like, and includes a hollow, externally tapered male input section 22, a hollow cylindrical female output section 23, and a bore 24, 25 extending therebetween. A crown 26 is integrally formed upon the top outer surface of connector 21, as shown. The internal diameter of bore 25 of the female output section 23 is of standard, uniform size, namely fifteen millimeters.

Figure 3:
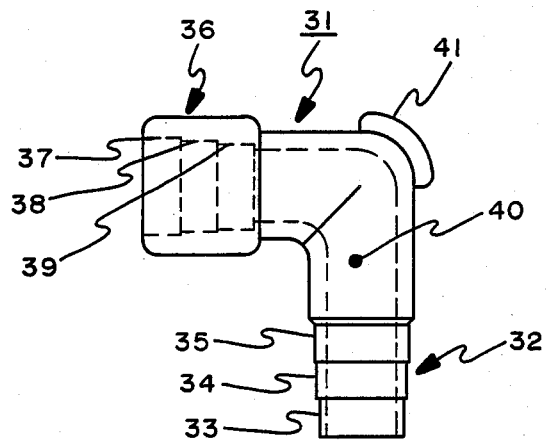
FIG. 3 is a side view of the improved breathing circuit connector of the present invention.

FIG. 3 illustrates one embodiment of the improved breathing circuit connector 31 of the present invention. Connector 31 includes a hollow, cylindrical male input section 32 having a series of three different outer diameter portions 33, 34 and 35; a hollow, cylindrical female output section 36, having a series of three different internal diameter or bore portions 37, 38, 39 and a bore 40 extending between the bore portion 39 and the open end of male input section 32. A crown 41 formed integrally with the connector appears at the outer apex of the connector.

Each of the series of outer diameter portions 33, 34 and 35 of male input section 32 are of uniform diameter and differ, slightly, from each other. The first or outermost diameter portion 33 adjacent the input end is slightly smaller than the third or innermost diameter portion 35; the second or intermediate diameter portion 34 is of larger diameter than first portion 33 and of smaller diameter than the third or innermost portion 34. The male input section 32, with its series of outer diameter portions 33, 34 and 35, is substantially identical to the male input section of the improved endotracheal tube connector of my above-mentioned U.S. Pat. No. 4,369,991.

Each of the series of three different internal diameter or bore portions 37, 38 and 39 of output section 36 are of uniform diameter and differ slightly from each other. The first or outermost internal diameter bore portion 37 adjacent the output end is slightly larger than the third or innermost internal diameter bore portion 39. The second or intermediate internal diameter bore portion 38 is of slightly smaller diameter than bore portion 37 and is slightly larger than the third bore portion 39.

The series of outer diameter portions 33, 34 and 35 differ one from the other by a relatively small amount, i.e., in the neighborhood of two-to four-thousandths of an inch, or about 0.05 to 0.1 millimeter. Similarly, the series of internal bore portions 37, 38 and 39 differ one from the other by similar amounts. It will be appreciated, therefore, that the illustrations of these portions in FIG. 3 are not necessarily drawn to scale and are, in fact, shown to be larger than these relatively small amounts for the purpose of illustration.

Figure 4:
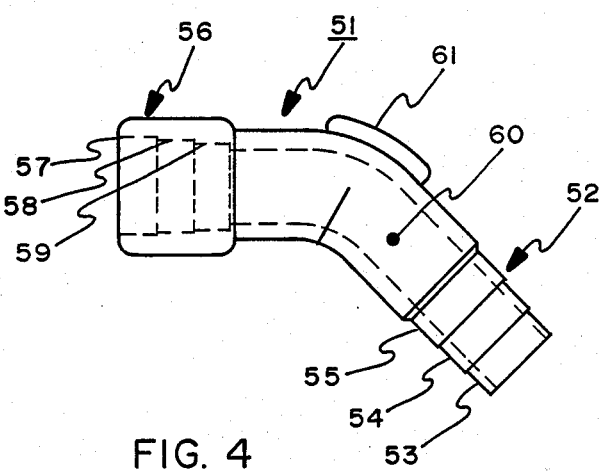
FIG. 4 is a side view of an alternative breathing circuit connector of the present invention.

The embodiment of the invention illustrated in FIG. 4 shows the improved breathing circuit connector 51 having a hollow, cylindrical male input section 52, a hollow, cylindrical female output section 56, and a bore 60 extending therebetween. A series of three different outer diameter portions 53, 54 and 55 appear upon the outer cylindrical surface of male input section 52. A series of three different internal diameter portions 57, 58 and 59 appear within the inner cylindrical surface of female output section 56. Crown 61 is formed integrally upon the outer surface of the connector, as shown.

The dimensions of the outer diameter portions 53, 54 and 55 upon the outer cylindrical surface of male input section 52 correspond to those of the outer diameter portions 33, 34 and 35 of connector 31 of FIG. 3. Similarly, the dimensions of the internal diameter portions 57, 58 and 59 correspond to those of the internal diameter portions 37, 38 and 39 of connector 31 of FIG. 3.

The endotracheal tube connector of my abovementioned U.S. Pat. No. 4,369,911, illustrated in FIG. 5, consists of a hollow, cylindrical input section 71, a hollow, cylindrical output section 72, a central flange portion 73 and a bore 74 extending therethrough. The outer cylindrical surface of input section 71 consists of three slightly reduced diameter portions in steps, as shown. The diameter of cylindrical portion 77 adjacent the input opening is smaller than the diameter of cylindrical portion 78, which, in turn, is slightly smaller than the diameter of cylindrical portion 79. The cylindrical output section 72 is shown installed over the open proximal end 76 of a conventional endotracheal tube 75, as described in U.S. Pat. No. 4,369,911.

Figure 6:
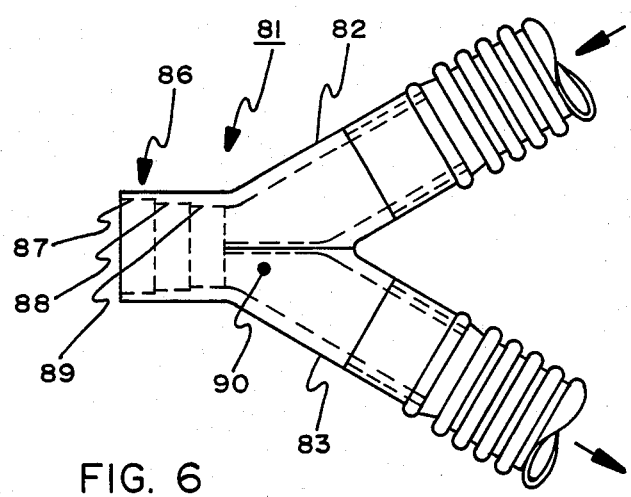
FIG. 6 is a side view of an alternative Y-type breathing circuit connector in accordance with the present invention.

The embodiment of the invention of FIG. 6 shows a breathing circuit connector 81 having a pair of hollow, cylindrical male sections 82 and 83 in the shape of a Y. The upper section 82 is securely coupled, as by cementing, to a corrugated or flexible hose from the anesthesiology machine. This upper section 82 receives the anesthetizing gas, or oxygen, as the case may be, from the anesthesiology machine. The lower section 83, securely coupled to a second corrugated, flexible hose, returns the exhaled gases from the patient back to the anesthesiology machine. Both male sections 82 and 83 are smooth, untapered and of uniform external diameter.

A single, hollow female output section 86 includes a series of three different internal diameter or bore portions 87, 88 and 89. A bore 90 extends between the bore portion 89 and the pair of hollow, cylindrical male sections 82 and 83. The dimensions of the internal diameter portions 87, 88 and 89 correspond to those of the hollow, female output sections 36 and 56 of the connectors 31 and 51 of FIGS. 3 and 4.

Figure 5:
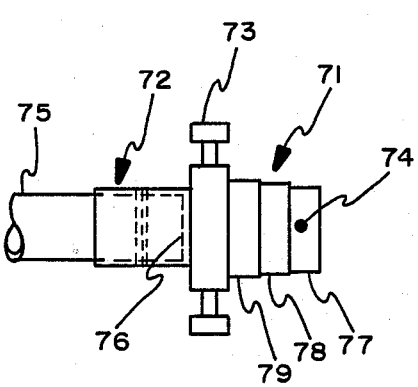
FIG. 5 is a side view of an improved endotracheal tube connector attached to the open proximal end of an endotracheal tube, as disclosed in my U.S. Pat. No. 4,369,991.

The hollow, female output sections 36 and 56, of the connectors 31 and 51 of FIGS. 3 and 4, are adapted for a secure air-tight coupling to the male input section 12 of the conventional endotracheal tube connector 11, of FIG. 1, or to the male input section 71 of the improved endotracheal tube connector of FIG. 5. It is preferred, however, that the improved breathing circuit connectors of the present invention be used with the improved endotracheal tube connector of FIG. 5.

The hollow, female output section 86, of the connector 81 of FIG. 6, is adapted for a secure and air-tight coupling to the male input section 22 of the conventional breathing circuit connector 21 of FIG. 2, or to the male input sections 32 and 52 of the connectors 31 or 51 of FIGS. 3 or 4. The hollow, female output section 86 of the connector 81 of FIG. 6 is also adapted for a secure, air-tight coupling directly to the hollow input section 71 of the improved endotracheal tube connector of FIG. 5.

An improved coupling is achieved between the female output sections 36, 56 and 86 of the breathing circuit connectors of the present invention and the male input sections of endotracheal tube connectors by virtue of the series of different internal diameter portions located within the hollow, female output sections. This improved coupling also exists between the female output section of the connector of FIG. 6 and the male imput section 32 or 52 of the connectors 31 or 51 of FIGS. 3 and 4. Since each of the internal diameter portions is uniform and untapered, and since each internal diameter portion differs slightly in diameter from its adjacent portion, a smooth and air-tight coupling can be achieved between at least one of the internal diameter portions with one of the smooth and untapered diameter portions of the male input section. For example, referring to FIGS. 5 and 6, the internal diameter portion 87 of female output section 86 may achieve a smooth and snug fit upon either the external diameter portion 77, or upon external diameter portion 78, or upon external diameter portion 79, depending, of course, upon the relative differences in the respective diameters of these diameter portions. Additionally, the internal diameter portion 88 of output section 86 may be found to fit smoothly upon external diameter portion 78. Finally, it may be found that internal diameter portion 89 of output section 86 will fit upon the external diameter portion 77, depending, of course, upon the relative diameters of these mating portions. Accordingly, it is noted that the diameters of each of the portions 87, 88 and 89 do not necessarily have to correspond to the diameters of portions 79, 78 and 77. It has been found that a snug and tight fit of any one of the internal diameter portions of the female output section with any one of the external diameter portions of the mating male input section achieves a secure and air-tight coupling.

Since each of the mating diameter portions is uniform and untapered, the forces normally found to exist in the conventional tapered sections tending to cause separation of the coupling do not exist in the improved connectors of the present invention. The improved connectors are generally molded of relatively hard plastic material, and by virtue of the several different diameter portions are capable of achieving an airtight coupling despite small variations in manufacturing tolerances which are likely to occur during manufacture.

Since many changes can be made in the above-described apparatus and many different embodiments of this invention could be made without departing from the scope thereof, it is intended that all matter contained in the above description or shown in the accompanying drawing shall be interpreted as illustrative and not in a limiting sense.

What is claimed is:

1. A breathing circuit connector for coupling the output from an anesthesiology machine to the open input end of an endotracheal tube connector, comprising in combination:
    (a) a body of relatively rigid material, said body having a hollow cylindrical input section adapted for coupling to the output of the anesthesiology machine, said body further having a hollow cylindrical output section adapted for coupling to the open input end of the endotracheal tube connector;
    (b) a passageway situated within said body and extending between and connecting said hollow cylindrical input and output sections for providing fluid coupling therebetween;
    (c) a first smooth and continuous cylindrical bore portion of uniform diameter situated within and forming an integral part of said hollow cylindrical output section, said first cylindrical bore portion having one end adjacent the output end of said hollow cylindrical output section and having a second end situated within said hollow cylindrical output section; and
    (d) a second smooth and continuous cylindrical bore portion of uniform diameter situated within and forming an integral part of said hollow cylindrical output section, said second cylindrical bore portion being coaxial with said first cylindrical bore portion and having one end adjacent the second end of said first cylindrical bore portion, said second cylindrical bore portion having a second end situated internally of said hollow cylindrical output section, the diameter of said first cylindrical bore portion being slightly larger than the diameter of said second cylindrical bore portion the difference between the diameter of said first bore portion and the diameter of said second bore portion being approximately 0.05 to 0.1 millimeter.

2. The breathing circuit connector as defined by claim 1 wherein the longitudinal axis of the first and second coaxial adjacent cylindrical bore portions situated within said cylindrical output section of said body is non-parallel with the longitudinal axis of said hollow cylindrical input section of said body.

3. The breathing circuit connector as defined by claim 2 wherein the angle between the longitudinal axis of the coaxial adjacent bore portions situated within said cylindrical output section of said body and the longitudinal axis of said hollow cylindrical input section of said body is approximately ninety degrees.

4. The breathing circuit connector as defined by claim 1 further comprising a third smooth and continuous cylindrical bore portion of uniform diameter situated within and forming an integral part of said hollow cylindrical output section, said third cylindrical bore portion being coaxial with said first and second cylindrical bore portions and having one end adjacent the second end of said second cylindrical bore portion, the diameter of said third cylindrical bore portion being slightly smaller than the diameter of said second cylindrical bore portion, the difference between the diameter of said third bore portion and the diameter of said second bore portion being approximately 0.05 to 0.1 millimeter, at least one of said first, second, or third cylindrical bore portions within said hollow cylindrical output section being adapted for achieving an airtight seal with the open input end of the endotracheal tube connector.

5. The breathing circuit connector as defined by claim 1 wherein said body of relatively rigid material having said hollow cylindrical input section and said hollow cylindrical output section has an additional hollow cylindrical section, and wherein said passageway situated within said body and extending between and connecting said hollow cylindrical input and output sections for providing fluid coupling therebetween also extends and connects to said additional hollow cylindrical section for providing fluid coupling between said hollow cylindrical input section, said hollow cylindrical output section and said additional hollow cylindrical section, said hollow cylindrical input section being adapted for coupling to the output of the anesthesiology machine for passing the anesthetizing gas or oxygen from the anesthesiology machine through said passageway to said hollow cylindrical output section, and said additional hollow cylindrical section being adapted for coupling to the input of the anesthesiology machine for returning exhaled gases passing through said hollow cylindrical output section and said passageway back to the anesthesiology machine.

6. In a breathing circuit connector for intercoupling between the output from an anesthesiology machine and the open input end of an endotracheal tube connector, said breathing circuit connector including a hollow cylindrical input section, a hollow cylindrical output section, and a passageway extending between and connecting said hollow cylindrical input and output sections for providing fluid coupling between the anesthesiology machine and the endotracheal tube connector, the improvement comprising:
   (a) a first smooth and continuous cylindrical bore portion of uniform diameter situated within and forming an integral part of said hollow cylindrical output section of said breathing circuit connector, said first cylindrical bore portion having one end adjacent the output end of said hollow cylindrical output section and having a second end situated within said hollow cylindrical output section;
   (b) a second smooth and continuous cylindrical bore portion of uniform diameter situated within and forming an integral part of said hollow cylindrical output section of said breathing circuit connector, said second cylindrical bore portion being coaxial with said first cylindrical bore portion and having one end adjacent the second end of said first cylindrical bore portion, said second cylindrical bore portion having a second end situated internally of said hollow cylindrical output section, the diameter of said first cylindrical bore portion being slightly larger than the diameter of said second cylindrical bore portion, the difference between the diameter of said first bore portion and the diameter of said second bore portion being approximately 0.05 to 0.1 millimeter, at least one of said first or second cylindrical bore portions situated within said hollow cylindrical output section being adapted for achieving an airtight seal with the open input end of the endotracheal tube connector.

* * * * *